(12) United States Patent
Broekhof et al.

(10) Patent No.: US 11,155,761 B2
(45) Date of Patent: Oct. 26, 2021

(54) SYNTHETIC ESTERS DERIVED FROM HIGH STABILITY OLEIC ACID

(71) Applicant: QUAKER CHEMICAL CORPORATION, Conshohocken, PA (US)

(72) Inventors: Nico Broekhof, Uithoorn (NL); Lex Herrendorf, Uithoorn (NL)

(73) Assignee: QUAKER CHEMICAL CORPORATION, Wilmington, DE (US)

( * ) Notice: Subject to any disclaimer, the term of this patent is extended or adjusted under 35 U.S.C. 154(b) by 3 days.

(21) Appl. No.: 15/573,721

(22) PCT Filed: May 18, 2016

(86) PCT No.: PCT/US2016/033056
§ 371 (c)(1),
(2) Date: Nov. 13, 2017

(87) PCT Pub. No.: WO2016/187288
PCT Pub. Date: Nov. 24, 2016

(65) Prior Publication Data
US 2018/0119043 A1 May 3, 2018

Related U.S. Application Data

(60) Provisional application No. 62/163,922, filed on May 19, 2015.

(51) Int. Cl.
*C10M 105/34* (2006.01)
*C10M 101/04* (2006.01)
(Continued)

(52) U.S. Cl.
CPC .......... *C10M 101/04* (2013.01); *C07C 67/08* (2013.01); *C10M 2207/023* (2013.01);
(Continued)

(58) Field of Classification Search
CPC .......... C10M 101/04; C10M 2207/026; C10M 2223/047; C10M 2207/2805;
(Continued)

(56) References Cited

U.S. PATENT DOCUMENTS 5,773,391 A 6/1998 Lawate et al.
6,180,575 B1 1/2001 Nipe
(Continued)

FOREIGN PATENT DOCUMENTS

EP 1741770 A1 7/2005
EP 2228425 A1 2/2009
WO 2016187288 A1 11/2016

OTHER PUBLICATIONS

"Petrofer Envolubric HE 46, HISAFE DU 46, Envolubric HE 68 and HISAFE DU 68 Hydraulic Fluids as Approved Industrial Fluids" Approval Report, Petrofer Chemie HR Fischer GmbH & Co. KG, Mar. 4, 2011, 10 pages.
(Continued)

*Primary Examiner* — Prem C Singh
*Assistant Examiner* — Francis C Campanell
(74) *Attorney, Agent, or Firm* — Morgan, Lewis & Bockius LLP

(57) ABSTRACT

A composition comprising a synthetic ester having a fatty acid mixture including: oleic acid in amount of at least about 85 wt % of the fatty acid mixture; linoleic acid in an amount of about 3 wt % of the fatty acid mixture or less; and linolenic acid in an amount of about 0.5 wt % of the fatty acid mixture or less.

9 Claims, 2 Drawing Sheets

(51) Int. Cl.
*C07C 67/08* (2006.01)
*C10N 30/02* (2006.01)
*C10N 30/08* (2006.01)
*C10N 30/10* (2006.01)
*C10N 40/08* (2006.01)
*C10N 70/00* (2006.01)

(52) U.S. Cl.
CPC ............... *C10M 2207/026* (2013.01); *C10M 2207/2805* (2013.01); *C10M 2207/2815* (2013.01); *C10M 2207/2835* (2013.01); *C10M 2207/401* (2013.01); *C10M 2209/104* (2013.01); *C10M 2215/064* (2013.01); *C10M 2215/223* (2013.01); *C10M 2223/045* (2013.01); *C10M 2223/047* (2013.01); *C10N 2030/02* (2013.01); *C10N 2030/08* (2013.01); *C10N 2030/10* (2013.01); *C10N 2040/08* (2013.01); *C10N 2070/00* (2013.01)

(58) Field of Classification Search
CPC .... C10M 2215/223; C10M 2207/2835; C10M 2223/045; C10M 2215/064; C10M 2209/104; C10M 2207/023; C10M 2207/2815; C10M 2207/401; C07C 67/08; C10N 2070/00
USPC .......................................................... 508/463
See application file for complete search history.

(56) References Cited

U.S. PATENT DOCUMENTS

| | | | | |
|---|---|---|---|---|
| 2006/0040833 | A1* | 2/2006 | Al-Akhdar | C10M 135/26 508/459 |
| 2006/0117648 | A1* | 6/2006 | Choo | C10L 10/08 44/389 |
| 2009/0038208 | A1 | 2/2009 | Despeghel | |
| 2012/0119862 | A1* | 5/2012 | Franklin | C12N 9/16 336/58 |
| 2013/0338385 | A1 | 12/2013 | Solazyme | |
| 2014/0377847 | A1 | 12/2014 | Franklin et al. | |
| 2015/0018260 | A1* | 1/2015 | Benecke | C07C 67/40 508/492 |
| 2018/0119043 | A1 | 5/2018 | Broekhof et al. | |

OTHER PUBLICATIONS

International Patent Application No. PCT/US2016/033056 Notification of Transmittal of International Search Report and Written Opinion of International Search Authority, dated Aug. 19, 2016, 8 pages.
International Patent Application No. PCT/US2016/033056 Notification Concerning Transmittal of International Preliminary Report on Patentability, dated Nov. 30, 2017, 7 pages.
European Patent Application 16797207.4 search report and written opinion dated Oct. 17, 2018, 9 pages.
Canadian Application 2986040 written opinion dated Oct. 28, 2018, 5 pages.
Canadian Application 2986040 written opinion dated Jul. 10, 2019, 5 pages.
Honary, An investigation of the use of soybean oil in hydraulic system, Bioresource Technology, 1996, vol. 56, pp. 41-47.
Office Action for corresponding Canadian Application No. 2,986,040 dated Apr. 7, 2021, 3 pages.
Examination Report for corresponding Canadian Patent Application No. 2,986,040 dated Sep. 25, 2020, 3 pages.
Office Action for corresponding European Patent Application No. 16 797 207.4 dated Nov. 23, 2020, 5 pages.

* cited by examiner

SYNTHETIC ESTERS DERIVED FROM HIGH STABILITY OLEIC ACID

CROSS-REFERENCE TO RELATED APPLICATIONS

This application is a U.S. National Stage Entry of International Patent Application Serial No. PCT/US2016/033056 filed May 18, 2016, entitled "Synthetic Esters Derived from High Stability Oleic Acid," which claims the benefit of U.S. Provisional Patent Application No. 62/163,922 filed May 19, 2015, entitled "Synthetic Esters Derived from High Stability Oleic Acid," each of which is incorporated by reference herein in their entireties.

BACKGROUND OF THE INVENTION

Triglycerides obtained from vegetable or animal sources are known to be used as base oil for lubricant formulations. These natural triglycerides often show poor hydrolytic stability as well as limited low temperature properties such as pour point and cold test stability. The present invention relates to synthetic esters prepared from, for example, an algal-derived triglyceride such as high stability algal oil from Solazyme Inc., which may provide excellent oxidation stability as well as improved low temperature properties and hydrolytic stability as compared to the corresponding triglycerides, making them suitable for a range of industrial lubricants.

SUMMARY OF THE INVENTION

According to some embodiments, the present invention relates to a composition comprising a synthetic ester having a fatty acid mixture comprising: oleic acid in amount of at least about 85 wt % of the fatty acid mixture; linoleic acid in an amount of about 3 wt % of the fatty acid mixture or less; and linolenic acid in an amount of about 0.5 wt % of the fatty acid mixture or less. In some embodiments, the linolenic acid is present in an amount of about 0.2 wt % of the fatty acid mixture or less.

In some embodiments, the synthetic ester is derived from high stability oleic acid. In some embodiments, the synthetic ester is derived from high stability algal oil.

In certain embodiments, the composition includes alcohol. In some embodiments the alcohol includes neo pentyl glycol (NPG), trimethylol propane (TMP), penta-erythritol (PE), di-TMP, di-PE, 2-ethyl hexanol, butyl ethyl propane diol (BEPD), trimethyl propanediol (TMPD), and/or propylene glycol.

In some embodiments, the composition meets standards for fire resistance according to Factory Mutual Approvals Class Number 6930, April 2009. In some embodiments, the composition maintains oxidative stability for about 2,500 hours or greater according to ASTM D943. In some embodiments, the composition exhibits a pour point temperature of about −10° C. or less.

In certain embodiments, the composition is a lubricant or a hydraulic fluid.

According to some embodiments, the present invention relates to a method of preparing a synthetic ester, comprising esterifying high stability oleic acid to produce a synthetic ester having a fatty acid mixture comprising: oleic acid in amount of at least about 85 wt % of the fatty acid mixture; linoleic acid in an amount of about 3 wt % of the fatty acid mixture or less; and linolenic acid in an amount of about 0.5 wt % of the fatty acid mixture or less.

BRIEF DESCRIPTION OF THE SEVERAL VIEWS OF THE DRAWINGS

The foregoing summary, as well as the following detailed description of certain embodiments of the invention will be better understood when read in conjunction with the following exemplary embodiments and the appended drawings.

DETAILED DESCRIPTION OF THE INVENTION

Figure 1:
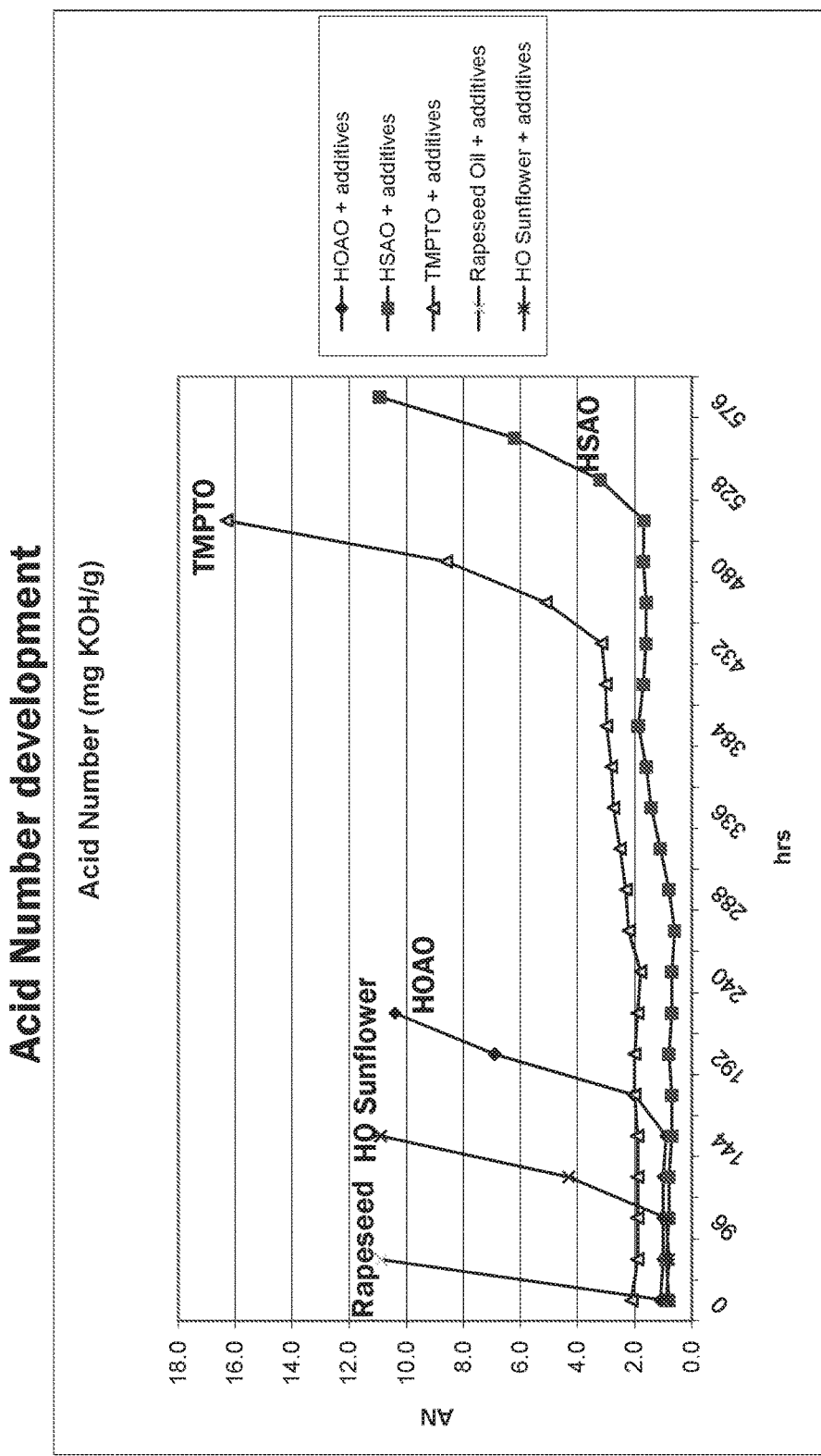
FIG. 1 is graph showing the varying acid number of esters including certain additives.

Compositions and methods of the present invention relate to synthetic esters derived from high stability oleic acid, which may be manufactured from high stability algal oil. In some embodiments, the synthetic esters have unique lubricant properties such as exceptional oxidation stability and/or improved low temperature properties as compared to the corresponding triglycerides.

Tailored triglycerides, e.g. obtained via genetically engineered plant seeds such as High Oleic Sunflower or High Oleic Canola, or genetically modified Algae, such as that manufactured by Solazyme, have been used in the past as a base oil for lubricant formulations. Specific triglycerides may provide beneficial properties such as oxidation stability, however, they may exhibit drawbacks such as limited low temperature properties including pour point and/or cold test stability.

Surprisingly, it has been found that a synthetic ester prepared from a triglyceride having a unique fatty acid distribution, such as high stability algal oil, may provide desirable lubricant properties including exceptional oxidation stability and superior low temperature properties compared with the corresponding triglyceride.

In some embodiments, the present invention relates to synthetic esters containing a) fatty acid mixtures with an oleic acid content of about 85 wt %, a linoleic acid content of about ≤3 wt % and a linolenic acid content of about ≤0.5 wt % relative to the mixture, b) alcohols, and c) as desired, polyfunctional carboxylic acids. Embodiments of the present invention also relate to industrial lubricants, such as hydraulic fluids, based on these esters.

Triglyceride

Compositions and methods of some embodiments of the present invention relate to triglycerides having a certain fatty acid distribution. In some embodiments, a suitable triglyceride may include high stability algal oil, such as that produced by Solazyme Inc.

In some embodiments, a suitable triglyceride may include a fatty acid mixture having oleic acid in amount of at least about 85 wt % of the fatty acid mixture; linoleic acid in an amount of about 3 wt % of the fatty acid mixture or less; and/or linolenic acid in an amount of about 0.5 wt % of the fatty acid mixture or less.

In some embodiments, a suitable triglyceride includes a fatty acid mixture having oleic acid in an amount of at least about 80 wt % of the fatty acid mixture; at least about 82 wt % of the fatty acid mixture; at least about 84 wt % of the fatty acid mixture; at least about 85 wt % of the fatty acid mixture; at least about 86 wt % of the fatty acid mixture; about 80 wt % to about 92 wt % of the fatty acid mixture;

about 82 wt % to about 90 wt % of the fatty acid mixture; about 84 wt % to about 88 wt % of the fatty acid mixture; about 85 wt % to about 87 wt % of the fatty acid mixture; about 80 wt % of the fatty acid mixture; about 82 wt % of the fatty acid mixture; about 84 wt % of the fatty acid mixture; about 86 wt % of the fatty acid mixture; about 88 wt % of the fatty acid mixture; about 90 wt % of the fatty acid mixture; or about 92 wt % of the fatty acid mixture.

In some embodiments, a suitable triglyceride includes a fatty acid mixture having linoleic acid in an amount of about 5 wt % of the fatty acid mixture or less; about 4 wt % of the fatty acid mixture or less; about 3 wt % of the fatty acid mixture or less; about 2 wt % of the fatty acid mixture or less; about 1 wt % of the fatty acid mixture or less; about 0.7 wt % of the fatty acid mixture or less; about 0.5 wt % of the fatty acid mixture or less; about 0.1 wt % to about 5 wt % of the fatty acid mixture; about 0.1 wt % to about 4 wt % of the fatty acid mixture; about 0.1 wt % to about 3 wt % of the fatty acid mixture; about 0.1 wt % to 2 wt % of the fatty acid mixture; about 0.1 wt % to about 1.5 wt % of the fatty acid mixture; about 0.1 wt % to about 1 wt % of the fatty acid mixture; about 0.2 wt % to about 0.8 wt % of the fatty acid mixture; about 0.2 wt % to about 0.6 wt % of the fatty acid mixture; about 0.1 wt % of the fatty acid mixture; about 0.2 wt % of the fatty acid mixture; about 0.3 wt % of the fatty acid mixture; about 0.4 wt % of the fatty acid mixture; about 0.5 wt % of the fatty acid mixture; about 0.6 wt % of the fatty acid mixture; about 0.8 wt % of the fatty acid mixture; about 1 wt % of the fatty acid mixture; about 1.5 wt % of the fatty acid mixture; about 2 wt % of the fatty acid mixture; about 3 wt % of the fatty acid mixture; about 4 wt % of the fatty acid mixture; or about 5 wt % of the fatty acid mixture.

In some embodiments, a suitable triglyceride includes a fatty acid mixture having linolenic acid in an amount of about 3 wt % of the fatty acid mixture or less; about 2 wt % of the fatty acid mixture or less; about 1 wt % of the fatty acid mixture or less; about 0.7 wt % of the fatty acid mixture or less; about 0.5 wt % of the fatty acid mixture or less; about 0.4 wt % of the fatty acid mixture or less; about 0.3 wt % of the fatty acid mixture or less; about 0.2 wt % of the fatty acid mixture or less; about 0.1 wt % of the fatty acid mixture or less; about 0 wt % to about 5 wt % of the fatty acid mixture; about 0.1 wt % to about 5 wt % of the fatty acid mixture; about 0 wt % to about 4 wt % of the fatty acid mixture; about 0 wt % to about 3 wt % of the fatty acid mixture; about 0 wt % to 2 wt % of the fatty acid mixture; about 0 wt % to about 1.5 wt % of the fatty acid mixture; about 0 wt % to about 1 wt % of the fatty acid mixture; about 0 wt % to about 0.8 wt % of the fatty acid mixture; about 0 wt % to about 0.6 wt % of the fatty acid mixture; about 0 wt % to about 0.4 wt % of the fatty acid mixture; about 0 wt % to about 0.2 wt % of the fatty acid mixture; about 0.1 wt % to about 4 wt % of the fatty acid mixture; about 0.1 wt % to about 3 wt % of the fatty acid mixture; about 0.1 wt % to 2 wt % of the fatty acid mixture; about 0.1 wt % to about 1.5 wt % of the fatty acid mixture; about 0.1 wt % to about 1 wt % of the fatty acid mixture; about 0.2 wt % to about 0.8 wt % of the fatty acid mixture; about 0.2 wt % to about 0.6 wt % of the fatty acid mixture; about 0.1 wt % of the fatty acid mixture; about 0.2 wt % of the fatty acid mixture; about 0.3 wt % of the fatty acid mixture; about 0.4 wt % of the fatty acid mixture; about 0.5 wt % of the fatty acid mixture; about 0.6 wt % of the fatty acid mixture; about 0.8 wt % of the fatty acid mixture; about 1 wt % of the fatty acid mixture; about 1.5 wt % of the fatty acid mixture; about 2 wt % of the fatty acid mixture; about 3 wt % of the fatty acid mixture; about 4 wt % of the fatty acid mixture; or about 5 wt % of the fatty acid mixture.

In some embodiments, a suitable triglyceride includes a fatty acid mixture having palmitoleic acid in an amount of about 5 wt % of the fatty acid mixture or less; about 4 wt % of the fatty acid mixture or less; about 3 wt % of the fatty acid mixture or less; about 2 wt % of the fatty acid mixture or less; about 1 wt % of the fatty acid mixture or less; about 0.7 wt % of the fatty acid mixture or less; about 0.5 wt % of the fatty acid mixture or less; about 0.1 wt % to about 5 wt % of the fatty acid mixture; about 0.1 wt % to about 4 wt % of the fatty acid mixture; about 0.1 wt % to about 3 wt % of the fatty acid mixture; about 0.1 wt % to 2 wt % of the fatty acid mixture; about 0.1 wt % to about 1.5 wt % of the fatty acid mixture; about 0.1 wt % to about 1 wt % of the fatty acid mixture; about 0.2 wt % to about 0.8 wt % of the fatty acid mixture; about 0.2 wt % to about 0.6 wt % of the fatty acid mixture; about 0.1 wt % of the fatty acid mixture; about 0.2 wt % of the fatty acid mixture; about 0.3 wt % of the fatty acid mixture; about 0.4 wt % of the fatty acid mixture; about 0.5 wt % of the fatty acid mixture; about 0.6 wt % of the fatty acid mixture; about 0.8 wt % of the fatty acid mixture; about 1 wt % of the fatty acid mixture; about 1.5 wt % of the fatty acid mixture; about 2 wt % of the fatty acid mixture; about 3 wt % of the fatty acid mixture; about 4 wt % of the fatty acid mixture; or about 5 wt % of the fatty acid mixture.

In some embodiments, a suitable triglyceride includes a fatty acid mixture having palmitic acid in an amount of about 4 wt % to about 14 wt % of the fatty acid mixture; about 6 wt % to about 12 wt % of the fatty acid mixture; about 8 wt % to about 10 wt % of the fatty acid mixture; about 4 wt % of the fatty acid mixture; about 6 wt % of the fatty acid mixture; about 8 wt % of the fatty acid mixture; about 9 wt % of the fatty acid mixture; about 10 wt % of the fatty acid mixture; about 12 wt % of the fatty acid mixture; or about 14 wt % of the fatty acid mixture.

In some embodiments, a suitable triglyceride includes a fatty acid mixture having stearic acid in an amount of about 1 wt % to about 6 wt % of the fatty acid mixture; about 2 wt % to about 5 wt % of the fatty acid mixture; about 3 wt % to about 4 wt % of the fatty acid mixture; about 1 wt % of the fatty acid mixture; about 2 wt % of the fatty acid mixture; about 3 wt % of the fatty acid mixture; about 4 wt % of the fatty acid mixture; about 5 wt % of the fatty acid mixture; or about 6 wt % of the fatty acid mixture.

Fatty Acid

The fatty acids in the triglyceride can be obtained by standard techniques known to those skilled in the art. For example, HSAO triglyceride may be split into glycerol and fatty acid (HSAO fa), which may be converted to many synthetic esters, including, neo pentyl glycol or NPG-ester, trimethylol propane or TMP-ester and penta-erythritol or PE-ester.

Alcohols

In some embodiments, a synthetic ester of the present invention comprises alcohol. In some embodiments, the fatty acids obtained from the triglyceride are converted with alcohol to prepare a synthetic ester. Selection of a suitable alcohol may provide improved properties, such as low temperature properties, of the synthetic ester in comparison to the corresponding triglyceride.

In some embodiments, alcohols that may be used for esterification include, but are not limited to neo pentyl glycol (NPG), trimethylol propane (TMP), and/or penta-erythritol (PE). In some embodiments, complex esters may be prepared by using, for example, dimer acid, adipic acid, and/or dodecanoic acid.

In some embodiments, suitable alcohols may include isopropanol, neo pentyl glycol (NPG), trimethylol propane (TMP), penta-erythritol (PE), di-TMP, di-PE, 2-ethyl hexanol, butyl ethyl propane diol (BEPD), trimethyl propanediol (TMPD), and/or propylene glycol.

In some embodiments, suitable alcohols may include 2-ethyl-2-(hydroxymethyl)-1,3-propanediol (trimethylol propane, TMP), 2,2-dimethyl-1,3-propanediol (neopentyl glycol, NPG), 2,2-bis(hydroxymethyl)-1,3-propanediol (pentaerythritol, penta), 2-butyl-2-ethyl-1,3-propanediol (BEPD), 2,2,4-trimethyl-1,3-propanediol (TMPD), polyglycerine, 2,2-diethyl-1,3-propanediol, 1,3,-propanediol, 1,2-propanediol (propylene glycol), 1,6-hexanediol, 1,4-butanediol, 1,4-butenediol, 1,4-butynediol, 1,2-cyclohexanediol, 1,4-cyclohexanediol, 1,2-, 1,3-, 1,4-, 1,8-, 2,4-, 2,7-, and 4,5-octanediol, tricyclodecane dimethanol (octahydro-4,7-methano-1-H-indenedimethanol, TCD Alcohol DM), 1,4-cyclohexanedimethanol (1,4-bis-(hydroxymethyl)-cyclohexane), 1,12-dodecanediol, 2-methyl-2,4-pentanediol (hexylene glycol), 2-methyl-1,3-propanediol (MPD), 2-methyl-1,2-propanediol, 2-hydroxyethoxy-ethan-2-ol (diethylene glycol), dipropylene glycol (3 isomer mixture), di-pentaerythritol, tri-pentaerythritol, di-trimethylolpropane (di-TMP), triethylene glycol, tri-propylene glycol, tetraethylene glycol, tetrapropylene glycol, polyethylene glycol (PEG, MW 200-1.000.000 gram/mol), polypropylene glycol (PPG, MW 200-10.000 gram/mol), ethane-1,2-diol (ethylene glycol), 1,2,-, 1,3-, 2,3-butanediol, 1,1-, 1,3-, 1,4-, 2,3- and 2,4-, pentanediol, 2-butene-1,2-diol, 2-butene-1,4-diol, 2-methyl-1,5-pentanediol, 2,4-dimethyl-2,4-pentanediol, 2,2-diethyl-1,4-butanediol, 2-pentene-1,5-diol, 2-propyl-1,3-butanediol, 1,4-hexanediol, 1,6-hexanediol, 5-methyl-1,2-hexanediol, 1-phenyl-1,2-ethanediol, 2-phenyl-1,2-propanediol, 1,6-diphenyl-1,6-hexanediol, 1,2-diphenyl-1,2-ethanediol, tris(2-hydroxyethyl)isocyanurate (THEIC), poly-tetrahyfrofuran (poly-THF, MW 250, 650, 1000, 1400, 1800 and 2000), 2-ethyl-1,3-hexanediol (EHD), EO-PO block copolymers, EO-PO-EO block copolymers, PO-EO block copolymers, PO-EO-PO block copolymers (so called "reverse" types), 1,2-pentanediol, 4-methyl-1,4-hexanediol, 3,3-dimethyl-1,6-hexanediol, 2,4-dimethyl-3-hexene-2,5-diol, 2,3-, 2,4-, 2,5-, and 3,4-hexanediol, 1,2,3,6-hexanetetrol, 2-heptene-1,6-diol, 5-ethyl-3-methyl-2,4-heptanediol, 2-methyl-2-octene-1,4-diol, 2,4,4,5,5,7-hexamethyl-3,6-octanediol, 2,7-dimethyl-4-octane-2,7-diol, 2-butyl-4-ethyl-3-methyl-1,3-octanediol, 1,9-nonanediol, 1,2- and 1,10-decanediol, 5-decyne-4,7-diol, 5,8-diethyl-6,7-dodecanediol, 9-octadecene-1,12-diol, 9,10 and 1,12-octadecanediol, 1,9- and 1,11-undecanediol, 1,13-tridecanediol,1,2-tetradecanediol, 1,2- and 1,16-hexadecanediol, 1,2- or 1,12-octadecanediol, 2-Isobutyl-1,3-propanediol, 2-ethyl-1,3-propanediol, 2-ethyl-1,3-butanediol, 2,2-diethyl-1,4-butanediol, 2,2,3,3,-tetramethyl-1,4-butanediol, bisphenol A, hydrogenated bisphenol A, ortho,meta or para-xylene-alpha, alpha diols, 3,6-dimethyl-ortho-xylene-alpha,alpha-diol, alpha,alpha,-dimethyl-para-xylene-alpha,alpha diol, 1,6-diphenyl-1,6-hexanediol, alkanolamines such as: triethanolamine (TEA), diethanolamine (DEA), N,N-dimethylaminoethanol, N,N-diethylaminoethanol, N,N-dibutylaminoethanol, N-phenyl-diethanolamine, N-methyl-diethanolamine, di-isopropyl-ethanolamine (mixture of isomers); 2-ethyl-2-(hydroxymethyl)-1,3-propanediol ethoxylates (trimethylol propane, TMP $EO_x$ where x ranges from 1 to 100 moles of EO), 2-ethyl-2-(hydroxymethyl)-1,3-propanediol propoxylates (Trimethylol propane, TMP, $PO_x$, where x ranges from 1-100 moles of PO), 2-Ethyl-2-(hydroxymethyl)-1,3-propanediol (random) Alkoxylates (Trimethylol propane, TMP E $O_x$-$PO_y$, TMP $EO_x$-$PO_y$-$EO_x$, reverse types like TMP $PO_x$-$EO_y$, TMP $PO_x$-$EO_y$-$PO_x$, where x and y range from 1-100 moles both for ethylene oxide (EO) and propylene oxide (PO), 2-ethyl-2-(hydroxymethyl)-1,3-propanediol butoxylate (trimethylol propane, TMP $BuO_x$, where x ranges from 1-25 moles of butyleneoxide), 2,2-dimethyl-1,3-propanediol ethoxylates (neopentyl glycol, NPG $EO_x$, where x ranges from 1 to 100 moles of EO), 2,2-dimethyl-1,3-propanediol propoxylates (neopentyl glycol, NPG $PD_x$, where x ranges from 1 to 100 moles of PO), 2,2-dimethyl-1,3-propanediol (random) alkoxylates (neopentyl glycol, NPG $EO_x$-$PO_y$, NPG $PO_x$-$EO_y$, NPG $EO_x$-$PO_y$-$EO_x$, reverse types like NPG $PO_x$-$EO_y$-$PO_x$ where x and y range from 1 to 100 moles for both ethylene oxide (EO) and propylene oxide (PO), 2,2-dimethyl-1,3-propanediol butoxylate (neopentyl glycol, NPG $BuO_x$, where x ranges from 1 to 25 moles of butyleneoxide), 2,2-bis(hydroxymethyl)-1,3-propanediol ethoxylates (pentaerythritol, penta $EO_x$, where x ranges from 1-100 moles of EO), 2,2-bis(hydroxymethyl)-1,3-propanediol propoxylates (pentaerythritol, penta $PO_x$, where x ranges from 1-100 moles of propyleneoxide (PO), 2,2-bis(hydroxymethyl)-1,3-propanediol (random) alkoxylates (pentaerythritol, penta $EO_x$-$PO_y$ where x and y range from 1-100 moles of EO and PO), 2,2-bis(hydroxymethyl)-1,3-propanediol $EO_x$-$PO_y$-$EO_x$ (pentaerythritol, penta $EO_x$-$PO_y$-$EO_x$, where x and y range from 1-100 moles of EO and PO), 2,2-bis(hydroxymethyl)-1,3-propanediol butoxylates (pentaerythritol, penta $BuO_x$, where x ranges from 1-25 moles of butyleneoxide), 2-butyl-2-ethyl-1,3-propanediol (BEPD) ethoxylates (BEPD $EO_x$, where x ranges from 1-100 moles of EO), 2-butyl-2-ethyl-1,3-propanediol (BEPD) propoxylates (BEPD $PD_x$, where x ranges from 1-100 moles of PO), 2-butyl-2-ethyl-1,3-propanediol (BEPD) (random) alkoxylates (BEPD EOx-POy, BEPD EOx-POy-EOx, BEPD POx-EOy-POx, where x ranges from 1-100 moles of EO and PO), and/or 2-butyl-2-ethyl-1,3-propanediol (BEPD) butoxylates (BEPD $BuO_x$, where x ranges from 1-25 moles of butyleneoxide).

Method

For example, HSAO triglyceride may be split into glycerol and fatty acid (HSAO fa), which may be converted to many synthetic esters, including, NPG-ester, TMP-ester and PE-ester. In some embodiments, the fatty acids obtained from the triglyceride are converted with alcohol to prepare a synthetic ester. These synthetic esters can be obtained by standard techniques known to those skilled in the art.

Product/Additional Components

In some embodiments, compositions comprising synthetic esters of the present invention may be used for lubricants. In some embodiments, compositions comprising synthetic esters of the present invention may be used for hydraulic fluids. Synthetic esters prepared according to embodiments of the present invention are understood to have the same fatty acid distribution as the corresponding triglyceride from which they were derived. In some embodiments, the fatty acid distribution of the compositions comprising synthetic esters of the present invention may be associated with desirable lubricant properties.

Compositions including synthetic esters of the present invention may include selected additional ingredients in suitable amounts to achieve the desired result. In some embodiments, compositions may include phenolic and/or aminic anti-oxidants, extreme pressure additives, anti-wear additives, viscosity modifiers, dewatering agents, emulsifiers, defoamers, and/or wetting agents. Depending on the type of composition to be prepared and the desired properties, some or all of the following components may be included in suitable amounts:

| Component | Exemplary Amount |
| --- | --- |
| Phenolic anti-oxidant | 0.1-3.0 wt % |
| Aminic anti-oxidant | 0.1-3.0 wt % |
| Extreme pressure additive | 0.05-1.0 wt % |
| Anti-wear additive | 0.05-1.0 wt % |
| Viscosity modifiers | 0.0-10 wt % |
| Dewatering agents | 0.0-0.2 wt % |
| Emulsifiers | 0.0-10.0 wt % |
| Defoamers | 0.0-0.2 wt % |
| Wetting agents | 0.0-3.0 wt % |

In some embodiments, suitable phenolic antioxidants may include alkylated monophenols, bis-hydroxyphenols, bisphenols, tris and tetraphenolics, thioester antioxidants, aminic antioxidants, and/or phosphite antioxidants.

In some embodiments, suitable alkylated monophenols may include 2,4-di-tert-butylphenol, 2,6-di-tert-butylphenol, 2,6-di-tert-butyl-4-methylphenol (BHT), 2-tert-4,6-di-methylphenol, di-sec-butylphenol, 2-sec-4-tert-butylphenol, 2,4-di-tert-amylphenol, 2,4-di-cumylphenol, 2,4,6-tri-tert-butylphenol, 2-tert-butylphenol, (1,1-dimethyl)-4-methoxyphenol, 2,6-di-tert-butyl-4-ethylphenol, 2,6-di-tert-butyl-4-n-butylphenol, 2,6-di-tert-butyl-4-hydroxymethylphenol, 2,6-di-tert-butyl-4-iso-butylphenol, 2,6-di-octadecyl-4-methylphenol, n-octadecyl-beta-4-hydroxy-3,5-di-tert-butylhydroxyphenyl)propionate, isotridecyl-3-(3,5-di-tert-butyl-4-hydroxyphenyl)propionate, iso-octyl-3-(3,5-di-tert-butyl-4-hydroxyphenyl)propionate, 2,6-di-tert-butyl-4-(N, N-dimethylaminomethyl)phenol, 3,5-di-tert-butyl-4-hydroxybenzylphosphonate-diethyl ester, 4,6-Bis (octylthiomethyl)-ortho-cresol, 2,4-bis(n-octylthio)-6-(4-hydroxy-3,5-di-tert-butylanilino)-1,3,5-triazine, and/or styrenated phenol (=mono or di or tri-alphamethylbenzyl-phenol).

In some embodiments, suitable bis-hydroxyphenols may include 2-(1,1-dimethylethyl)-1,4-benzenediol, 2,5-di-tert-butyl-hydroquinone, 2,5-di-tert-amylhydroquinone, and/or 2,6-diphenyl-4-octadecyloxyphenol.

In some embodiments, suitable bisphenols may include 2,2-methyl enebis-(6-tert-butyl-4-methylphenol), 2,2-methylenebis-(4-ethyl-6-tert-butylphenol), 4,4-methylenebis-(2, 6-di-tert-butylphenol), 4,4-butylidenebis-(3-methyl-6-tert-butylphenol), triethyleneglycol-bis[3-(3-tert-butyl-4-hydroxy-5-methylphenyl)propionate], 2,2-methylenebis-[4-methyl-6-(alpha-methylcyclohexyl)-phenol], 2,2-methylenebis-(4-methyl-6-cyclohexylphenol), 2,2-methylenebis-(6-nonyl-4-methylphenol), 1,6-hexanediol-bis[3-(3,5-di-tert-butyl-4-hydroxyphenylpropionate], 4,4-thiobis(3-methyl-6-tert-butylphenol), bis-(3,5-di-tert-butyl-4-hydroxybenzyl)sulphide, 2,2-thiodiethylene-bis[3-(3,5-di-tert-butyl-4-hydroxyphenyl)propionate], N.N-hexamethylene-bis-(3,5-di-tert-butyl-4-hydroxy)hydrocinnamide, 2,2-ethylidenebis-(4,6-di-tert-butylphenol), 1,2-bis[3,5-di-tert-butyl-4-hydroxyhydrocinnamoyl]hydrazine, 2,2-methylenebis-(4,6-di-tert-butylphenol), 2,2-ethylidenebis-(4,6-di-tert-butylphenol), 2,2-ethylidenebis-(6-tert-butyl-para-isobutylphenol), 2,2-methylenebis46-(alpha-methylbenzyl)-4-nonylphenol, 4,4-methylenebis-(6-tert-butyl-2-methylphenol), 1,1-bis-(5-tert-butyl-4-hydroxy-2-methylphenyl)butane, 2,6-di-(-3-tert-butyl-5-methyl-2-hydroxybenzyl)-4-methylphenol, 2,2-methylene-bis-(6-(1-methylcyclohexyl-para-cresol), 2,2-oxamidobis[ethyl-3-(3, 5-di-tert-butyl-4-hydroxyphenyl)-propionate, and/or 6, 6-di-tert-butyl-2,2-thiobis-para-cresol.

In some embodiments, suitable tris and tetraphenolics may include tris-(3,5-di-tert-butylhydroxybenzyl)isocyanurate, 1,3,5-trimethyl-2,4,6-tris(3,5-di-tert-butyl-4-hydroxybenzyl)benzene, tetrakis[methylene-3-(3,5-di-tert-butyl-4-hydroxyphenyl)propionate]methane, 1,1,1,-tris-(2-methyl-4-hydroxy-5-tert-butylphenol)butane, 1,3,5-tris-(4-tert-butyl-3-hydroxy-2,6-dimethylbenzyl)isocyanurate, 3,3-bis-(3-tert-butyl-4-hydroxyphenyl)-ethylenebutyrate, di-(3-tert-butyl-4-hydroxy-5-methylphenyl)-dicyclopentadiene, di-[2-(3-tert-butyl-2-hydroxy-5-methylbenzyl)-6-tert-butyl-4-methylphenyl]terephtalate, butylated reaction product of p-cresol and dicyclopentadiene.

In some embodiments, suitable thioester antioxidants may include pentaerythrityl-tetrakis(3-laurylpropionate), dilauryl-3,3-thiopropionate, distearyl-3,3-thiopropionate, di-tridecyl-3,3-thiopropionate, di-myristyl-3,3-thiopropionate, stearylthiopropionamide, bis[2-methyl-4-(3-n-$C_{12}$-$C_{14}$ alkylthiopropionyloxy)-5-tert-butylphenyl]sulphode, and/or di-octadecyldisulphide.

In some embodiments, suitable aminic antioxidants may include octyl/butyl-diphenylamine, p,p-bis-nonyl-diphenylamine, N-phenyl-1-diphenylamine, N-phenyl-2-diphenylamine, octylated-phenyl-alpha-naphtylamine, p,p-bis-octyl-diphenylamine, polymerized 2,2,4-trimethyl-1,2-dihydroquinoline, 4,4-bis-(alpha,alpha-dimethylbenzyl)-diphenylamine, N, N-di-2-naphtyl-p-phenylenediamine, N,N-diphenyl-p-phenylenediamine, N-phenyl-N-isopropyl-p-phenylenediamine, N-phenyl-N-(1,3-dimethylbutyl)-p-phenylenediamine, N-(1-methylheptyl)-N-phenyl-p-phenylenediamine, mixed diaryl-p-phenylenediamine (Wingstay 100), N,N-di-sec-butyl-para-phenylenediamine, N,N-di-iso-propyl-para-phenylenediamine, N,N-bis-(1,4-dimethylpentyl)-para-phenylenediamine, N,N-bis-(1-ethyl-3-methylpentyl)-para-phenylenediamine, N,N-dicyclohexyl-para-phenylenediamine, N,N-diphenyl-para-phenylenediamine, N-isopropyl-N-phenyl-para-phenylenediamine, N,N-di-sec-butyl-para-phenylenediamine, N-cyclohexyl-N-phenyl-para-phenylenediamine, N,N-dimethyl-N,N-di-sec-butyl-para-phenylenediamine, diphenylamine, and/or 2,4-diaminodiphenyl methane.

In some embodiments, suitable phosphite antioxidants may include tris-(2,4-di-tert-butylphenyl)-phosphite, tris-(n-nonylphenyl)-phosphite, diphenyl-iso-octyl-phosphite, diphenyl-isodecyl-phosphite, diphenyl-mono-tridecyl-phosphite, phenyl-di-isodecyl-phosphite, tris-(2-ethylhexyl)-phosphite, tris(isodecyl) phosphite, tris(tridecyl) phosphite, tri-laurylthio-phosphite, tris-(mono & di nonylphenyl mixed) phosphites, bis-(2,4-di-tert-butylphenyl) pentaerythritol, and/or di stearylpentaerythritol diphosphite.

In some embodiments, a composition may include a yellow metal passivator. In some embodiments, suitable yellow metal passivators may include beznotriazole, tolutriazole, triazole, 2-mercaptobenzothiazole, 2,5-dimercaptothiadiazole, tetrahydrobenzotriazole, Irgamet 39© (BASF), Irgamet 42© (BASF), and/or Irgamet 30© (BASF).

Use

In some embodiments, synthetic esters of the present invention are prepared and/or formulated to provide improved properties, such as low temperature properties, of the synthetic ester in comparison to the corresponding triglyceride. Synthetic esters prepared from a triglyceride having a unique fatty acid distribution as described herein, such as high stability algal oil, may provide desirable lubricant properties including exceptional oxidation stability and superior low temperature properties compared with the corresponding triglyceride. As a result, such synthetic esters may be useful in metal lubricants and/or hydraulic fluids, and metal lubricants and/or hydraulic fluid containing such synthetic esters may exhibit improved properties as well.

In some embodiments, compositions including synthetic esters of the present invention meet standards for fire resistance according to Factory Mutual Approvals Class Number 6930, April 2009, which standard is incorporated by reference herein in its entirety.

In some embodiments, compositions including synthetic esters of the present invention maintain oxidative stability for about 750 hours or greater according to ASTM D943, which standard is incorporated by reference herein in its entirety. In some embodiments, compositions including synthetic esters of the present invention maintain oxidative stability according to ASTM D943 for about 200 hours or greater; about 250 hours or greater; about 300 hours or greater; about 350 hours or greater; about 400 hours or greater; about 450 hours or greater; about 500 hours or greater; about 550 hours or greater; about 600 hours or greater; about 650 hours or greater; about 700 hour or greater; about 750 hours or greater; about 800 hours or greater; about 850 hours or greater; about 900 hours or greater; about 950 hours or greater; about 1000 hours or greater; about 1100 hours or greater; about 1200 hours or greater; about 1300 hours or greater; about 1400 hours or greater; about 1500 hours or greater; about 1600 hours or greater; about 1700 hours or greater; about 1800 hours or greater; about 1900 hours or greater; about 2000 hours or greater; about 2100 hours or greater; about 2200 hours or greater; about 2300 hours or greater; about 2400 hours or greater; about 2500 hours or greater; about 200 hours to about 3000 hours; about 500 hours to about 3000 hours; about 750 hours to about 3000 hours; about 750 hours to about 2500 hours; about 800 hours to about 2000 hours; about 1000 hours to about 1800 hours; about 1200 hours to about 1600 hours; about 200 hours; about 800 hours; about 900 hours; about 1000 hours; about 1200 hours; about 1400 hours; about 1600 hours; about 1800 hours; about 2000 hours; about 2200 hours; about 2400 hours; or about 2500 hours.

In some embodiments, compositions including synthetic esters of the present invention exhibit a pour point temperature of about −10° C. or less. In some embodiments, compositions including synthetic esters of the present invention exhibit a pour point temperature of about 0° C. or less; about −5° C. or less; about −10° C. or less; about −15° C. or less; about −20° C. or less; about −25° C. or less; about −30° C. or less; about −35° C. or less; about −40° C. or less; about −45° C. or less; about −50° C. or less; about 0° C.; about −5° C.; about −10° C.; about −15° C.; about −20° C.; about −25° C.; about −30° C.; about −35° C.; about −40° C.; about −45° C.; about −50° C.; about −10° C. to about −70° C.; about −10° C. to about −50° C.; about −15° C. to about −65° C.; about −20° C. to about −60° C.; about −25° C. to about −55° C.; about −30° C. to about −50° C.; or about −35° C. to about −45° C.

In some embodiments, compositions including synthetic esters of the present invention exhibit a cloud point temperature of about −10° C. or less. In some embodiments, compositions including synthetic esters of the present invention exhibit a pour point temperature of about 0° C. or less; about −5° C. or less; about −10° C. or less; about −15° C. or less; about −20° C. or less; about −25° C. or less; about −30° C. or less; about −35° C. or less; about −40° C. or less; about −45° C. or less; about −50° C. or less; about 0° C.; about −5° C.; about −10° C.; about −15° C.; about −20° C.; about −25° C.; about −30° C.; about −35° C.; about −40° C.; about −45° C.; about −50° C.; about −10° C. to about −70° C.; about −10° C. to about −50° C.; about −15° C. to about −65° C.; about −20° C. to about −60° C.; about −25° C. to about −55° C.; about −30° C. to about −50° C.; or about −35° C. to about −45° C.

As used throughout, the term "about" is understood to mean±10% of the value referenced. For example, "about 90" is understood to literally mean 81 to 99.

The Oxidation Tests followed the following protocol:
Dry-TOST test: ASTM D 943, ISO 4263
Test sample: 330 ml
Oxidation bath temperature 95.5° C. (204° F.)
$O_2$ flow 3 liter/hour, 0.4 bar inlet pressure
Catalyst: Copper-Iron coil
Initial measurement of acid number and viscosity, t=0 situation
Sampling at regular intervals for AN and viscosity
'Lifetime' (hrs) is reached when the initial AN has increased with 2.0 mg KOH/g
Reproducibility (at tight variable control): ±5% (hrs)
Latest revision: Appearance rating of catalyst coil wires
Tests were performed without additives, and also with a fixed (hydraulic fluid) additive package as set forth below, including:
0.25% Aminic AO
0.50% Phenolic AO
0.10% Cu-corrosion inhibitor
0.25% Thiophosphate AW additive
0.05% Defoamer Results of the Dry-TOST without additives are set forth in the chart below:

| Product | Dry TOST Lifetime (hrs) | Acidity (mg KOH/g) | Details 24 hr check ΔAN/ ΔViscosity 40° C. | Details 48 hr check ΔAN/ ΔViscosity 40° C. |
|---|---|---|---|---|
| HOAO | <24 | 0.43 | 4.4/31 | 10/72 |
| HSAO | <24 | 0.06 | 2.6/19 | 8.7/51 |
| TMPTO | 31 | 1.38 | 2.2/35 | 6.4/71 |
| Rapeseed Oil | <24 | 0.19 | 3.3/36 | 6.3/113 |
| HO Sunflower | <24 | 0.12 | 6.9/48 | 6.9/48 |

Figure 2:
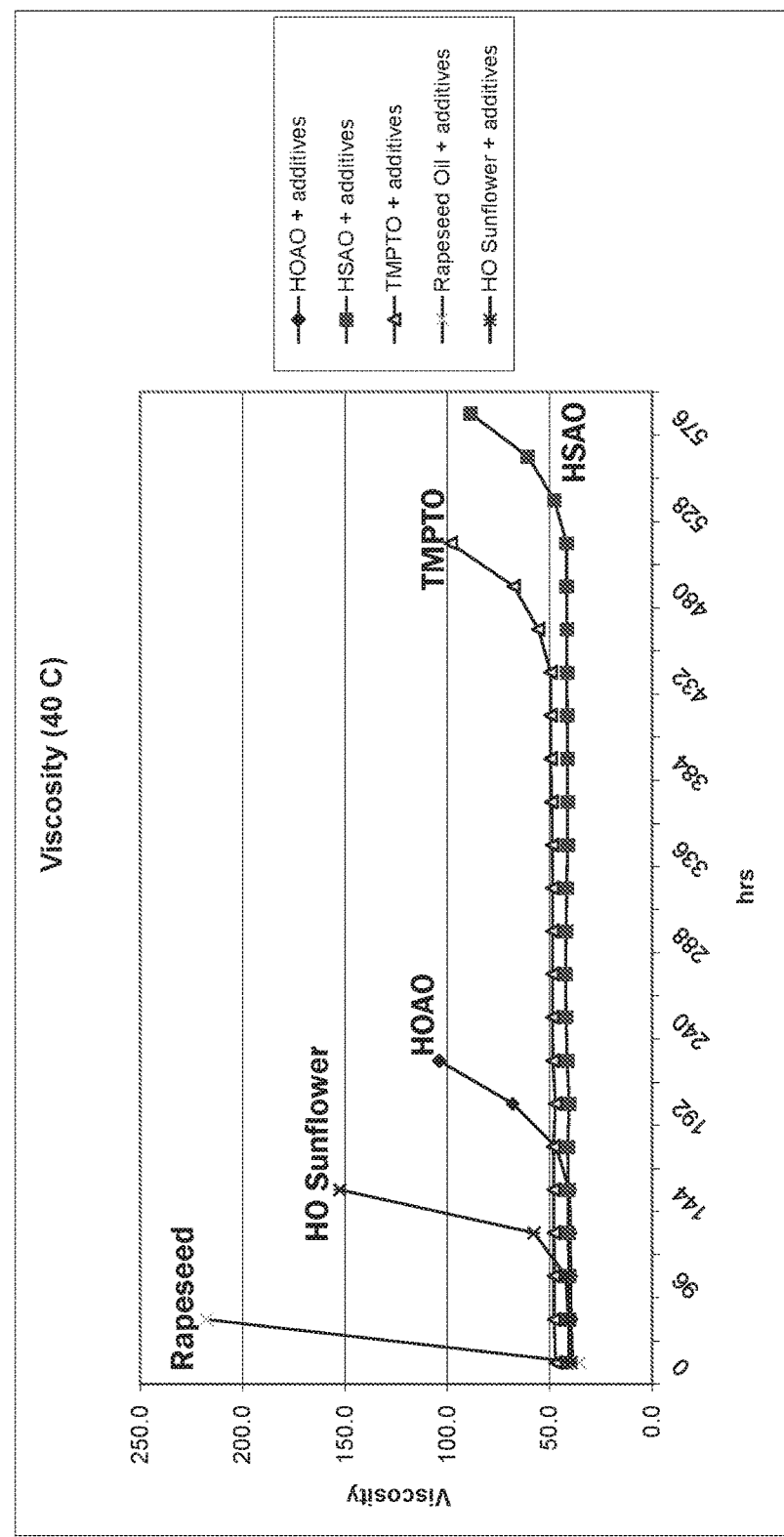
FIG. 2 is a graph showing the varying viscosity of esters including certain additives.

Results of the Dry-TOST with additives are set forth in the chart below and FIG. 1 and FIG. 2:

| Product | Lifetime (hrs) |
|---|---|
| HOAO + additives | 176 |
| HSAO + additives | 513 |
| TMPTO + additives | 438 |
| Rapeseed Oil + additives | <72 |
| HO Sunflower + additives | 113 |

High Oleic Algal Oil (HOAO) and High Stability Algal Oil (HSAO) were evaluated in comparison to Trimethylolpropane tri-oleate (TMPTO), Rapeseed Oil and High Oleic Sunflower Oil. The test profile included: fatty acid distribution, viscosities/VI, Flash- and Fire point, Cloud point, Pour point, and Cold test (e.g., the temperature when solid after 24 hours, in 5° C. steps).

The viscosities and viscosity indices of the products are set forth in the chart below:

| Product | Viscosity at 40° C. | Viscosity at 100° C. | VI |
|---|---|---|---|
| HOAO | 38.91 | 8.49 | 204 |
| HSAO | 40.32 | 8.64 | 200 |
| TMPTO | 46.44 | 9.44 | 193 |
| Rapeseed Oil | 35.01 | 8.06 | 215 |
| HO Sunflower | 39.57 | 8.57 | 203 |

The flash and fire point of the products are set forth in chart below:

| Product | Flash Point (° C.) | Fire Point (° C.) |
|---|---|---|
| HOAO | 326 | 362 |
| HSAO | 326 | 366 |
| TMPTO | 316 | 362 |
| Rapeseed Oil | 326 | 360 |
| HO Sunflower | 332 | 362 |

The cloud point, pour point and cold test of the products are set forth in the chart below:

| Product | Cloud Point (° C.) ISL MPP5G | Pour Point (° C.) ISL MPP5G | Cold Test (° C.) 24 hrs/−5° C. steps |
|---|---|---|---|
| HOAO | −13 | −24 | Solid at −10 |
| HSAO | −14 | −18 | Solid at −10 |
| TMPTO | −26 | −51 | Liquid at −30 |
| Rapeseed Oil | −15 | −21 | Solid at −15 |
| HO Sunflower | −13 | −18 | Solid at −10 |

In some embodiments, the following pour point depressants were used, with the impact noted in the chart below:

| Pour Point Depressants | Supplier | Treat Rates (%) Recommended | Treat Rates (%) Actual |
|---|---|---|---|
| Viscoplex 10-171 | Evonik | 0.25-0.5 | 0.25-5.0 |
| Viscoplex 10-312 | Evonik | 0.25-0.5 | 0.25-0.5 |
| Functional PPD-555 | Functional Products | 0.5-1.0 | 0.5-1.0 |
| Functional PPD-557 | Functional Products | 0.5-1.0 | 0.5-1.0 |
| Lubrizol 3702 | Lubrizol | 0.2-2.0 | 0.2-2.0 |
| Lubrizol 3715 | Lubrizol | 0.2-2.0 | 0.2-2.0 |

Pour point decrease: 5° C. max (at 4-5% treat rate)

In some embodiments, HSAO-based Synthetic Esters, when evaluated in hydraulic fluids, include the following non-optimized additive package:

| | |
|---|---|
| Cu-corrosion inhibitor | 0.10 |
| Mono-phenolic AO | 0.50 |
| Aminic AO | 0.35 |
| EP/AW-agent | 0.25 |
| Dewatering agent | 0.02 |
| Anti-foam | 0.05 |

The properties of certain oleic acid types are set forth in the charts below:

| | Fatty acid distributions of various Oleic acid types Typical values | |
|---|---|---|
| Carbon chain distribution | Oleic acid vegetable origin | HSAO fatty acid algal origin |
| C 12 | 0.5 | 0.1 |
| C 14 | 0.3 | 0.4 |
| C 16 | 5.7 | 4.1 |
| C 16:1 | — | 0.1 |
| C 18 | 2.1 | 3.4 |
| C 18:1 | 78.8 | 88.8 |
| C 18:2 | 11.8 | 1.8 |
| C 18:3 | 0.1 | 0.2 |
| C 20 | 0.3 | 0.3 |
| C 20:1 | 0.5 | 0.5 |

| | | Esters - Standard Oleic Acid | | |
|---|---|---|---|---|
| Parameters | UOM | NPG-DO Clear light amber liquid | TMP-TO Clear yellow to amber liquid | Penta-TO Clear yellow liquid |
| Appearance | visual | | | |
| Acid number | mgKOH/g | 0.4 | 1.1 | 1.4 |
| Viscosity 40° C. | mm2/s | 24.4 | 46.7 | 72.1 |
| Viscosity 100° C. | mm2/s | 5.84 | 9.3 | 13 |
| Viscosity index | mm2/s | 198 | 187 | 184 |
| Pour point | ° C. | −21 | −36 | −21 |
| Flash point (COC) | ° C. | 262 | 315 | 314 |

| | | Esters - HSAO Fatty Acid | | |
|---|---|---|---|---|
| Parameters | UOM | NPG-VHOA Clear light yellow liquid | TMP-VHOA Clear yellow liquid | Penta-VHOA Clear yellow liquid |
| Appearance | visual | | | |
| Acid number | mgKOH/g | 1.45 | 1.2 | 1.4 |
| Viscosity 40° C. | mm2/s | 25.7 | 47.5 | 68.3 |
| Viscosity 100° C. | mm2/s | 6.26 | 9.42 | 12.84 |
| Viscosity index | mm2/s | 210 | 187 | 191 |
| Pour point | ° C. | −21 | −27 | −24 |
| Flash point (COC) | ° C. | 274 | 320 | 312 |

Dry-TOST Results

| Raw Material | ISO 25 % | ISO 25 % | ISO 46 % | ISO 46 % | ISO 68 % | ISO 68 % |
|---|---|---|---|---|---|---|
| NPG Di-HSAO ester | 98.73 | | | | | |
| NPG-DO | | 98.73 | | | | |
| TMP Tri-HSAO ester | | | 98.73 | | | |
| TMP-TO | | | | 98.73 | | |
| Penta Tetra-HSAO ester | | | | | 98.73 | |
| PETO | | | | | | 98.73 |
| Additive package | 1.27 | 1.27 | 1.27 | 1.27 | 1.27 | 1.27 |
| Total, %: | 100.00 | 100.00 | 100.00 | 100.00 | 100.00 | 100.00 |

| Dry-TOST test | Acid Number (mg KOH/g) | | | | | |
|---|---|---|---|---|---|---|
| t = 0 hrs | 2.10 | 1.45 | 2.05 | 1.94 | 2.03 | 1.81 |
| t = 96 hrs | 1.95 | 1.40 | 1.93 | 1.91 | 1.92 | 1.45 |
| t = 144 hrs | 1.88 | 1.34 | 1.82 | 1.88 | 1.84 | 1.49 |
| t = 336 hrs | 1.82 | 1.34 | 1.51 | 1.78 | 1.72 | 4.86 |
| t = 480 hrs | 1.68 | 16.4 | 1.54 | 1.75 | 1.40 | — |
| t = 600 hrs | 1.38 | — | 1.42 | 14.1 | 1.40 | — |
| t = 792 hrs | | | | | | |
| Life time, hours | | 356 | | 501 | | 277 |

Ester overview for the patent
All esters made with Soleum Very High Oleic Acid (SVHOA)

| Raw material | ISO 25 % | ISO 25 % | ISO 46 % | ISO 46 % | ISO 68 % | ISO 68 % |
|---|---|---|---|---|---|---|
| NPG-Di SVHOA ester | 98.73 | | | | | |
| NPG-DO | | 98.73 | | | | |
| TMP-Tri-SVHOA ester | | | 98.73 | | | |
| TMP-TO | | | | 98.73 | | |
| Penta Tetra SVHOA ester | | | | | 98.73 | |
| PETO | | | | | | 98.73 |
| Tolutriazole | 0.10 | 0.10 | 0.10 | 0.10 | 0.10 | 0.10 |
| 2,6-di-tert-Butylphenol | 0.50 | 0.50 | 0.50 | 0.50 | 0.50 | 0.50 |
| Irgalube 349* | 0.25 | 0.25 | 0.25 | 0.25 | 0.25 | 0.25 |
| Irganox L 57* | 0.35 | 0.35 | 0.35 | 0.35 | 0.35 | 0.35 |
| EO-PO Block copolymer | 0.02 | 0.02 | 0.02 | 0.02 | 0.02 | 0.02 |
| Clerol AMH 2* | 0.05 | 0.05 | 0.05 | 0.05 | 0.05 | 0.05 |
| Total, %: | 100.00 | 100.00 | 100.00 | 100.00 | 100.00 | 100.00 |

| Dry-TOST test | Acidnumber, mgKOH/g: | | | | | |
|---|---|---|---|---|---|---|
| t = 0 hrs | 2.10 | 1.45 | 2.05 | 1.94 | 2.03 | 1.81 |
| t = 96 hrs | 1.95 | 1.40 | 1.93 | 1.91 | 1.92 | 1.45 |
| t = 144 hrs | 1.88 | 1.34 | 1.82 | 1.88 | 1.84 | 1.49 |
| t = 336 hrs | 1.82 | 1.34 | 1.51 | 1.78 | 1.72 | 4.86 |
| t = 480 hrs | 1.68 | 16.4 | 1.54 | 1.75 | 1.40 | — |
| t = 600 hrs | 1.38 | | 1.42 | 14.1 | 1.66 | |
| Life time, hours | | 356 | | 501 | | 277 |

*Irgalube 349 is a trade mark of BASF/Ciba
*Irganox L-57 is a trade mark of BASF/Ciba
*Clerol AMH 2 is a trade mark of BASF/Ciba
*NPG-DO, TMP-TO and PETO are esters made in-house at Quaker Chemical B.V.

EXAMPLES

Example 1

Various triglycerides and esters were analyzed for fatty acid distribution. The results are included in the chart below:

| | Fatty Acid Distribution (Typical values) | | | | | | |
|---|---|---|---|---|---|---|---|
| Product | C16 | C16:1 | C18 | C18:1 | C18:2 | C18:3 | Other |
| HOAO | 3.5 | 0 | 3.2 | 83.8 | 7.8 | .4 | 1.3 |
| High stability algal oil | 8.8 | 0.4 | 3.3 | 86.2 | 0.4 | 0 | 0.9 |
| TMPTO* | 5.3 | 1.8 | 1.9 | 76.8 | 10.7 | 0 | 3.5 |
| Rapeseed Oil | 4.5 | .2 | 2 | 63.9 | 18 | 8.6 | 2.8 |
| HO Sunflower | 4.0 | 0.1 | 3.6 | 83.8 | 6.3 | 0.2 | 2 |

*Ester prepared from standard oleic acid (not high stability algal oil);
HOAO very similar to HO Sunflower (as intended);
Rapeseed oil: high unsaturation;
HSAO: high Oleic, but near-zero C18:2 and C18:3;
TMPTO: relatively high in C18:2.

It is understood that esters prepared from the triglycerides listed above will have the same fatty acid distribution as the corresponding triglyceride.

The test results above demonstrate the effectiveness of the formulation in providing desirable levels of corrosion protection and paint adhesion.

While illustrative embodiments and examples of the invention are disclosed herein, it will be appreciated that numerous modifications and other embodiments may be devised by those skilled in the art and that these embodiments and examples are non-limiting. For example, the features for the various embodiments can be used in other embodiments. Therefore, it will be understood that the appended claims are intended to cover all such modifications and embodiments that come within the spirit and scope of the present disclosure.

A number of references have been cited, the entire disclosures of which are incorporated herein in their entirety by reference.

We claim:

1. A composition comprising:
   a) synthetic ester in about 58.6 wt % to about 99.7 wt % of the composition,
      wherein the synthetic ester is an esterification reaction product prepared from a fatty acid mixture and an alcohol;
      wherein the fatty acid mixture comprises
         i. oleic acid in an amount of at least about 85 wt. % of the fatty acid mixture,
         ii. linoleic acid in an amount of about 3 wt. % of the fatty acid mixture of less,
         iii. linolenic acid in an amount of about 0.5 wt. % of the fatty acid mixture or less, and
      wherein the alcohol is selected from the group consisting of trimethylol propane (TMP), neopentyl glycol (NPG), pentaerythritol (PE), 2-butyl-2-ethyl-1,3-propanediol (BEPD), 2,2,4-trimethyl-1,3-propanediol (TMPD), polyglycerol, 2,2-diethyl-1,3-propanediol, 1,3,-propanediol, 1,2-propanediol, 1,4-butanediol, 1,4-butenediol, 1,4-butynediol, 1,6-hexanediol, 1,2-cyclohexanediol, 1,4-cyclohexanediol, 1,2-, 1,3-, 1,4-, 1,8-, 2,4-, 2,7-, and 4,5-octanediol, tricyclodecane dimethanol (TCD), 1,4-cyclohexanedimethanol, 1,12-dodecanediol, 2-methyl-2,4-pentanediol, 2-methyl-1,3-propanediol (MPD), 2-methyl-1,2-propanediol, 2-hydroxyethoxy-ethan-2-ol, dipropylene glycol (3 isomer mixture), di-pentaerythritol, tri-pentaerythritol, di-trimethylolpropane (di-TMP), triethylene glycol, tri-propylene glycol, tetraethylene glycol, tetrapropylene glycol, polyethylene glycol (PEG, MW 200-1.000.000 g/mol), polypropylene glycol (PPG, MW 200-10.000 g/mol), ethylene glycol, 1,2,-, 1,3-, 2,3-butanediol, 1,1-, 1,3-, 1,4-, 2,3-, 2,4-pentanediol, 2-butene-1,2-diol, 2-butene-1,4-diol, 2-methyl-1,5-pentanediol, 2,4-dimethyl-2,4-pentanediol, 2,2-diethyl-1,4-butanediol, 2-pentene-1,5-diol, 2-propyl-1,3-butanediol, 1,4-hexanediol, 1,6-hexanediol, 5-methyl-1,2-hexanediol, 1-phenyl-1,2-ethanediol, 2-phenyl-1,2-propanediol, 1,6-diphenyl-1,6-hexanediol, 1,2-diphenyl-1,2-ethanediol, tris(2-hydroxyethyl)isocyanurate (THEIC), poly-tetrahyfrofuran (poly-THF, MW 250, 650, 1000, 1400, 1800 and 2000 g/mol), 2-ethyl-1,3-hexanediol (EHD), EO-PO block copolymers, EO-PO-EO block copolymers, PO-EO block copolymers, PO-EO-PO block copolymers, 1,2-pentanediol, 4-methyl-1,4-hexanediol, 3,3-dimethyl-1,6-hexanediol, 2,4-dimethyl-3-hexene-2,5-diol, 2,3-, 2,4-, 2,5-, 3,4-hexanediol, 1,2,3,6-hexanetetrol, 2-heptene-1,6-diol, 5-ethyl-3-methyl-2,4-heptanediol, 2-methyl-2-octene-1,4-diol, 2,4,4,5,5,7-hexamethyl-3,6-octanediol, 2,7-dimethyl-4-octane-2,7-diol, 2-butyl-4-ethyl-3-methyl-1,3-octanediol, 1,9-nonanediol, 1,2-, 1,10-decanediol, 5-decyne-4,7-diol, 5,8-diethyl-6,7-dodecanediol, 9-octadecene-1,12-diol, 9,10, 1,12-octadecanediol, 1,9-, 1,11-undecanediol, 1,13-tridecanediol, 1,2-tetradecanediol, 1,2-, 1,16-hexadecanediol, 1,2-, 1,12-octadecanediol, 2-isobutyl-1,3-propanediol, 2-ethyl-1,3-propanediol, 2-ethyl-1,3-butanediol, 2,2-diethyl-1,4-butanediol, 2,2,3,3,-tetramethyl-1,4-butanediol, bisphenol A, hydrogenated bisphenol A, ortho,meta, para-xylene-alpha, alpha diols, 3,6-dimethyl-ortho-xylene-alpha,alpha-diol, alpha,alpha-dimethyl-para-xylene-alpha,alpha diol, 1,6-diphenyl-1,6-hexanediol; 2-ethyl-2-(hydroxymethyl)-1,3-propanediol ethoxylates (TMP-EOx where x ranges from 1 to 100 moles of EO), 2-ethyl-2-(hydroxymethyl)-1,3-propanediol propoxylates (TMP-POx, where x ranges from 1-100 moles of PO), 2-ethyl-2-(hydroxymethyl)-1,3-propanediol (random) alkoxylates (TMP-EOx-POy, TMP-EOx-POy-EOx, TMP-POx-EOy, TMP-POx-EOy-POx, where x and y range from 1-100 moles both for EO and PO), 2-ethyl-2-(hydroxymethyl)-1,3-propanediol butoxylate (TMP-BuOx, where x ranges from 1-25 moles of BuO (butyleneoxide)), 2,2-dimethyl-1,3-propanediol ethoxylates (NPG-EOx, where x ranges from 1 to 100 moles of EO), 2,2-dimethyl-1,3-propanediol propoxylates (NPG-PDx, where x ranges from 1 to 100 moles of PO), 2,2-dimethyl-1,3-propanediol (random) alkoxylates (NPG-EOx-POy, NPG-POx-EOy, NPG-EOx-POy-EOx, NPG-POx-EOy-POx where x and y range from 1 to 100 moles for both EO and PO), 2,2-dimethyl-1,3-propanediol butoxylate (NPG-BuOx, where x ranges from 1 to 25 moles of BuO), 2,2-bis(hydroxymethyl)-1,3-propanediol ethoxylates (penta EOx, where x ranges from 1-100 moles of EO), 2,2-bis(hydroxymethyl)-1,3-propanediol propoxylates (penta POx, where x ranges from 1-100 moles of propyleneoxide (PO)), 2,2-bis(hydroxymethyl)-1,3-propanediol (random) alkoxylates (penta EOx-POy where x and y range from 1-100 moles of EO and PO), 2,2-bis(hydroxymethyl)-1,3-propanediol EOx-POy-EOx (penta EOx-POy-EOx, where x and y range from 1-100 moles of EO and PO), 2,2-bis(hydroxymethyl)-1,3-propanediol butoxylates (penta BuOx, where x ranges from 1-25 moles of butyleneoxide), 2-butyl-2-ethyl-1,3-propanediol (BEPD) ethoxylates (BEPD-EOx, where x ranges from 1-100 moles of EO), 2-butyl-2-ethyl-1,3-propanediol propoxylates (BEPD-POx, where x ranges from 1-100 moles of PO), 2-butyl-2-ethyl-1,3-propanediol (random) alkoxylates (BEPD-EOx-POy, BEPD-EOx-POy-EOx, BEPD-POx-EOy-POx, where x ranges from 1-100 moles of EO and PO), and 2-butyl-2-ethyl-1,3-propanediol butoxylates (BEPD-BuOx, where x ranges from 1-25 moles of butyleneoxide); and b) additives in a total amount of about 0.3 wt % to about 41.4 wt % of the composition, wherein the additives include phenolic anti-oxidant in an amount of 0.1-3.0 wt % of the composition and aminic anti-oxidant in an amount of 0.1- 3.0 wt % of the composition.

2. The composition of claim 1, wherein the alcohol is selected from the group consisting of neo pentyl glycol (NPG), trimethylol propane (TMP), penta-erythritol (PE), di-TMP, di-PE, 2-ethyl hexanol, butyl ethyl propane diol (BEPD), trimethyl propanediol (TMPD), and propylene glycol.

3. The composition of claim 1, wherein the linolenic acid is present in an amount of 0.2 wt. % of the fatty acid mixture or less.

4. The composition of claim 1, wherein the composition meets standards for fire resistance according to Factory Mutual Approvals Class Number 6930, April 2009.

5. The composition of claim 1, wherein the composition maintains oxidative stability for about 2,500 hours or greater according to ASTM D943.

6. The composition of claim 1, wherein the composition exhibits a pour point temperature of about −10° C. or less.

7. The composition of claim 1, wherein the alcohol is selected from the group consisting of neo pentyl glycol, trimethylol propane, and penta-erythritol.

8. The composition of claim 1, wherein the alcohol is trimethylol propane.

9. The composition of claim 1, wherein the fatty acid mixture is derived from cleaving of a high stability algal oil sourced from genetically modified algae.

* * * * *